US008741565B2

(12) United States Patent (10) Patent No.: US 8,741,565 B2
Gu et al. (45) Date of Patent: Jun. 3, 2014

(54) OLIGONUCLEOTIDE MICROARRAY FOR IDENTIFICATION OF PATHOGENS

(75) Inventors: Yuandong Gu, Plymouth, MN (US); Leon Xu, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 1861 days.

(21) Appl. No.: 11/617,563

(22) Filed: Dec. 28, 2006

(65) Prior Publication Data

US 2010/0279885 A1 Nov. 4, 2010

Related U.S. Application Data

(60) Provisional application No. 60/755,504, filed on Dec. 30, 2005.

(51) Int. Cl.
*C12Q 1/68* (2006.01)
*C07H 21/02* (2006.01)
*C07H 21/04* (2006.01)

(52) U.S. Cl.
USPC ......... 435/6.11; 435/6.1; 435/6.12; 536/23.1; 536/23.7; 536/24.2; 536/24.3; 536/24.33

(58) Field of Classification Search
USPC ................................ 435/6.1, 6.11, 6.12, 91.2
See application file for complete search history.

(56) References Cited

U.S. PATENT DOCUMENTS

| 6,150,517 | A | * | 11/2000 | Hogan et al. ............... 536/25.3 |
| 6,258,570 | B1 | * | 7/2001 | Glustein et al. ............ 435/91.2 |
| 6,268,147 | B1 | * | 7/2001 | Beattie et al. .................... 435/6 |
| 6,905,816 | B2 | | 6/2005 | Jacobs et al. |
| 2002/0142293 | A1 | * | 10/2002 | Crainic et al. .................... 435/5 |
| 2003/0091991 | A1 | | 5/2003 | Ezaki |
| 2003/0186222 | A1 | | 10/2003 | Paul, III |
| 2004/0072239 | A1 | * | 4/2004 | Renaud et al. ................. 435/7.1 |
| 2005/0079490 | A1 | | 4/2005 | Stuber et al. |
| 2006/0088844 | A1 | | 4/2006 | Xu |

FOREIGN PATENT DOCUMENTS

| EP | 1464710 | 10/2004 |
| EP | 1591544 | 11/2005 |
| WO | 8905359 | 6/1989 |
| WO | 2004033720 | 4/2004 |
| WO | 2004004365 | 6/2004 |
| WO | 2005100611 | 10/2005 |

OTHER PUBLICATIONS

Anthony et al. Rapid Diagnosis of Bacteremia by Universal Amplification of 23S Ribosomal DNA Followed by Hybridization to an Oligonucleotide Array. Journal of Clinical Microbiology (2000) 38(2): 781-788.*
Kotetishvili et al. Multilocus Sequence Typing for Characterization of Clinical and Environmental *Salmonella* Strains. Journal of Clinical Microbiology (2002) 40(5): 1626-1635.*
Baker et al. Review and re-analysis of domain-specific 16S primers. Journal of Microbiological Methods (2003) 55: 541-555.*
Ashelford et al. Primrose: a computer program for generating and estimating the phylogenetic range of 16S rRNA oligonucleotide probes and primers in conjunction with the RDP-II database. Nucleic Acids Research (2002) 30(15): 3481-3489.*
Wilson et al. Sequence-specific identification of 18 pathogenic microorganisms using microarray technology. Molecular and Cellular Probes (2002) 16: 119-127.*
Aono et al., "Detection of Human Alpha-herpesvirus DNA Using Consensus Primers and Specific Probes," Scandanavian University Press, ISSN 0365-5237, Suppl. 514, pp. 132-134, 1994.
Chapman et al., "Molecular Detection and Identification of Enteroviruses Using Enzymatic Amplification and Nucleic Acid Hybridization," Journal of Clinical Microbiology, vol. 28, No. 5, pp. 843-850, May 1990.
Edman et al., "Pathogen Analysis and Genetic Predisposition Testing Using Microelectronic Arrays and Isothermal Amplification," Journal of Investigative Medicine, vol. 48, No. 2, pp. 93-101, Mar. 2000.
Greisen et al., "PCR Primers and Probes for the 16S rRNA Gene of Most Species of Pathogenic Bacteria, Including Bacteria Found in Cerebrospinal Fluid," Journal of Clinical Microbiology, vol. 32, No. 2, pp. 335-351, Feb. 1994.
Korimbocus et al., "DNA Probe Array for the Simultaneous Identification of Herpesviruses, *Enteroviruses*, and Flaviviruses," Journal of Clinical Microbiology, vol. 43, No. 8, pp. 3779-3787, Aug. 2005.
Liu et al., "Development and Evaluation of 16S rDNA Microarray for Detecting Bacterial Pathogens in Cerebrospinal Fluid," Society for Experimental Biology and Medicine, pp. 587-591, 2005.
Loy et al., "ProbeBase: an Online Resource for rRNA-targeted Oligonucleotide Probes," Nucleic Acids Research, vol. 31, No. 1, pp. 514-516, 2003.
Lu et al., "Use of PCR with Universal Primers and Restriction Endonuclease Digestions for Detection and Identification of Common Bacterial Pathogens in Cerebrospinal Fluid," Journal of Clinical Microbiology, vol. 38, No. 6, pp. 2076-2080, Jun. 2000.
Romero, "Reverse-Transcription Polymerase Chain Reaction Detection of the *Enteroviruses*," Arch Patol Lab Me, vol. 123, Dec. 1999, pp. 1161-1169.
Wang et al., "Design and Evaluation of Oligonucleotide-microarray Method for the Detection of Human Intestinal Bacteria in Fecal Samples," FEMS Microbiology Letters, vol. 213, pp. 175-182, 2002.

* cited by examiner

*Primary Examiner* — Ardin Marschel
(74) *Attorney, Agent, or Firm* — Seager, Tufte & Wickhem LLC

(57) ABSTRACT

A method for detecting a target nucleic acid of a pathogen in a test sample, the method comprising preparing a target nucleic acid detecting reagent and contacting the target nucleic acid detecting reagent with an oligonucleotide microarray. A kit for detecting a target nucleic acid of a pathogen in a test sample is also described. The kit comprises at least one primer pair and an oligonucleotide microarray comprising at least one probe.

8 Claims, 5 Drawing Sheets

```
                    <—————Primer 2————
        170            180              190
———>
AAGCACCGGCTAACTCCGTGCCAGCAGCCGCGGTAAT    Proteus
AAGCACCGGCTAACTCCGTGCCAGCAGCCGCGGTAAT    E. coli 2
AAGCACCGGCTAACTCCGTGCCAGCAGCCGCGGTAAT    E. coli
AAGCACCGGCTAACTCCGTGCCAGCAGCCGCGGTAAT    Salmonella
AAGCACCGGCTAACTCCGTGCCAGCAGCCGCGGTAAT    H. influenzae
AAGCACCGGCTAACTCCGTGCCAGCAGCCGCGGTAAT    M. tuberculosis
AAGCACCGGCCAACTACGTGCCAGCAGCCGCGGTAAT    N. meningitides
AAGCACCGGCTAACTACGTGCCAGCAGCCGCGGTAAT    Anaerobacter
AAGCCACGGCTAACTACGTGCCAGCAGCCGCGGTAAT    Enterococcus
AAGCCACGGCTAACTACGTGCCAGCAGCCGCGGTAAT    L. monocytogenes
AAGGGACGGCTAACTACGTGCCAGCAGCCGCGGTAAT    Streptococcus
AAGCCACGGCTAACTACGTGCCAGCAGCCGCGGTAAT    Staphylococcus
AAGCCACGGCTAACTATGTGCCAGCAGCCGCGGTAAT    Mycoplasma
AAGCACC GGCTAACTACGTGCCAGCAGCCGCGGTAAT   Leptospira
AAGCCCCGGCTAATTACGTGCCAGCAGCCGCGGTAAT    B. burgdorferi
```

Figure 1B

```
                        <---Primer 2---
      1530      1540      1550      1560
GTCTGGGTAATCTTGTTAAACCCTGTCGTCGTGCTGGGGATAGAGCAT   Coccidiodes immit

US 8,741,565 B2

OLIGONUCLEOTIDE MICROARRAY FOR IDENTIFICATION OF PATHOGENS

This application claims the benefit of U.S. Provisional Patent Application 60/755,504 filed Dec. 30, 2005.

BACKGROUND OF THE INVENTION

The present invention relates to test kits and methods for detecting the presence of a pathogen in a test sample. The test sample may be obtained from a patient or alternatively from a source of food or drink that may contain pathogens.

Diseases such as encephalitis, cephalomeningitis, meningitis, pneumonia, enterogastritis, endocarditis, urinary infectiosus, are caused by infection by a pathogen. The pathogens include different bacteria, viruses, fungi and protozoa. Different pathogenic infections commonly have similar symptoms resulting in difficulties in providing an accurate diagnosis of the cause of the infection or disease. For example, encephalitis and meningitis patients generally manifest fever, headache, and convulsion. Identifying the pathogens responsible for these symptoms quickly and accurately is important to determining which medication to prescribe. Current diagnostic procedures for identification of pathogens include microscopic examination, microbiological culturing, serum immunity test, and Polymerase Chain Reaction (PCR). These procedures require highly trained staff and are very time consuming.

According to the conventional PCR method, a test sample containing a gene functioning as a template is mixed with at least one pair of PCR primers designed so as to amplify at least one gene having a specific length. By subjecting the amplified PCR product to electrophoresis using agarose gel and staining it, the PCR product is visualized. According to the PCR method, the gene contained in the test sample is identified based on the length of the visualized PCR product. Multiple primer pairs can be amplified in the same sample in order to screen for multiple genes more efficiently.

However, as the number of PCR primers contained in a primer reagent is increased, "noise" on an electrophoresis gel is increased. "Noise" occurs when PCR products are produced due to non-specific annealing. For this reason, when a PCR reaction is used, it is difficult to determine the presence of more than only a few genes.

Additionally, it is necessary to design the primers so that the PCR products amplified by the PCR reaction are distinguishable on electrophoresis gels, which often have limited resolution. Designing PCR primers that produce suitably distinguishable PCR products with low noise is difficult and time consuming. Thus, a strictly PCR/electrophoresis-based approach is inefficient for screening for expression of a large number of genes.

SUMMARY OF THE INVENTION

The present invention relates to a method and a test kit for detecting a target nucleic acid in a biological sample or test sample. An oligonucleotide microarray is used for fast and high throughput screening for the presence of pathogens. The oligonucleotide microarray contains various oligonucleotides (probes) of known pathogens, and discriminates the pathogens in one hybridization assay.

In one aspect, the present invention relates to a method of easily and rapidly determining whether a polynucleotide containing a target nucleic acid is present in a biological sample or test sample.

In another aspect, the present invention relates to a method for detecting a target nucleic acid of a pathogen in a biological sample or test sample, the method comprising amplifying the target nucleic acid in the sample utilizing one or more primer pairs that bind conserved regions in more than one pathogen, contacting the amplified target nucleic acid with an oligonucleotide microarray, and detecting binding of target nucleic acids to the probes, where binding to a particular pathogen probe indicates the presence of that pathogen in the sample. The microarray includes two or more probes or sets of probes comprising polynucleotide sequences complementary to different pathogens.

In a further aspect, the invention relates to a method of distinguishing *E. coli* and *salmonella* in a sample. The method involves amplifying nucleic acids in the sample utilizing one or more primer pairs that bind conserved regions in *E. coli* and *salmonella*, contacting the amplified nucleic acids with an oligonucleotide microarray, and detecting binding of nucleic acids to the probes as an indication of the presence of *E. coli* and/or *salmonella* in the sample. The microarray includes two or more probes comprising polynucleotide sequences complementary to variable regions in *E. coli* and *salmonella*.

In another aspect, the present invention relates to a kit for detecting a target nucleic acid of a pathogen in a biological sample or test sample, the kit comprising at least one primer pair, and an oligonucleotide microarray comprising at least one probe immobilized on a solid support.

Other aspects and advantages of the present invention will become apparent from the following description, taken in conjunction with the accompanying drawings, illustrating by way of example the principles of the invention.

BRIEF DESCRIPTION OF THE DRAWING

FIGS. 1A and 1B show conserved primer regions and variable probe regions of bacterial DNA sequences of 16S rDNA, including SEQ ID NO: 1, 2, 13-15, 17-21, 23, 24, and 27-33.

FIGS. 2A and 2B show conserved primer regions and variable probe regions of fungi DNA sequences of 18S rDNA, including SEQ ID NO: 11 and 12.

DETAILED DESCRIPTION OF THE INVENTION

I. Pathogens

Figure 1A:
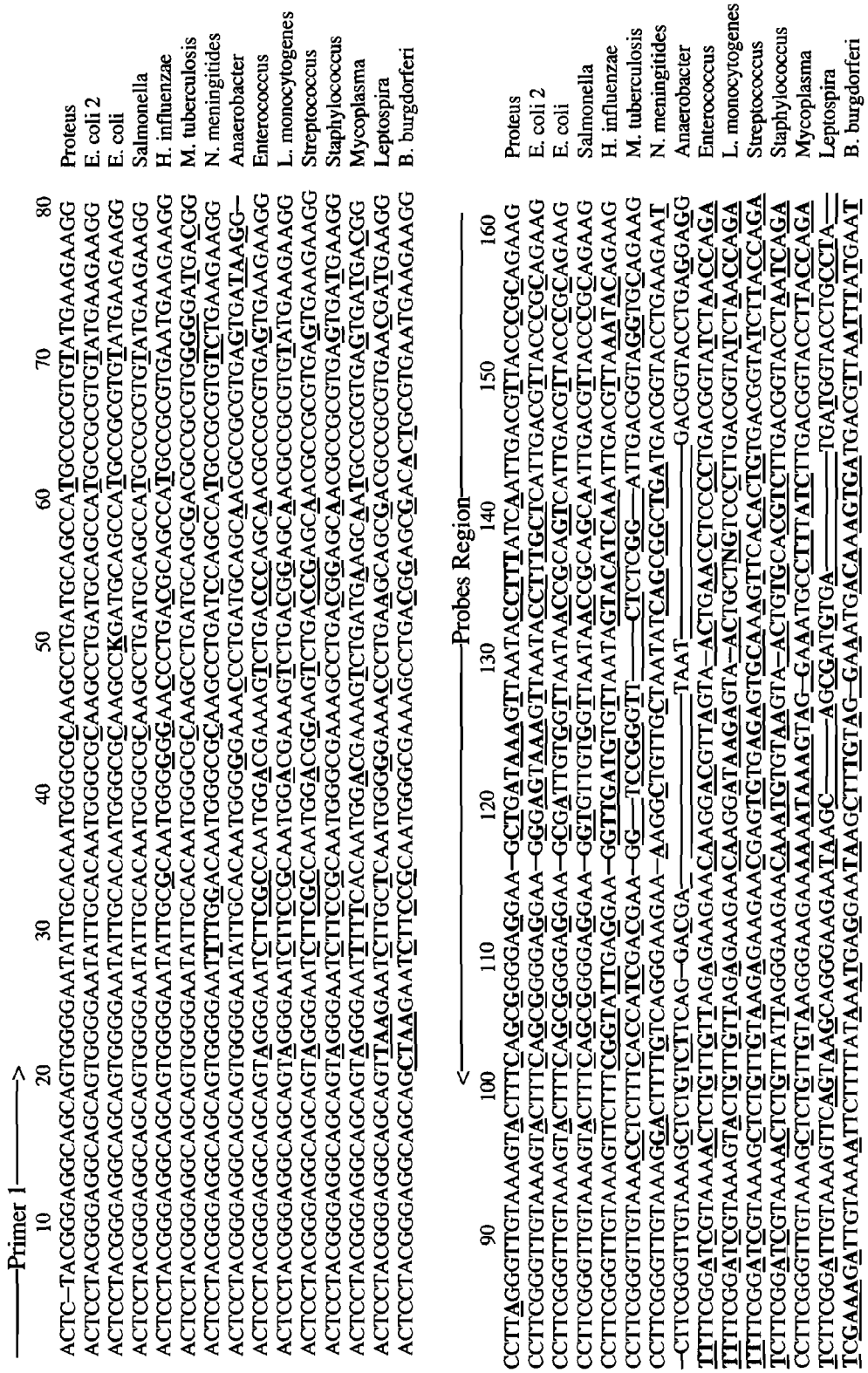

The term "pathogen" refers to an agent of disease or a disease producer. The term pathogen most commonly is used to refer to infectious organisms. These include, but are not limited to, bacteria, viruses, fungi, and protozoa. The methods and kits of the present invention are useful in identifying pathogens and microorganisms which have caused infectious disease or food poisoning. Examples of pathogens include, but are not limited to, *rickettsia, chlamydia, mycoplasma, spirochete, streptococcus, salmonella, staphylococcus, mycoplasma, L. monocytogenes, N. meningitides, E. coli, H. influenzae, B. burgdorferi, leptospira, proteus, anaerobacter, M. tuberculosis, enterococcus,* poliovirus 1, enterovirus 71, enterovirus 70, echovirus 2, echovirus 4, echovirus 6, echovirus 9, echovirus 11, echovirus 12, echovirus 26, coxsackievirus A13, coxsackievirus A15, coxsackievirus A18, coxsackievirus A20, coxsackievirus A21, coxsackievirus B3-A, coxsackievirus B3-C, HSV-1, and HSV-2.

II. Biological Samples and Test Samples

The term "biological sample", as used herein, refers to a sample obtained from an organism or from components (e.g., cells) of an organism. In one embodiment the organism is a mammal. In another embodiment, the organism is a human. The sample may be of any biological tissue or fluid. Frequently the biological sample will be a derived from a patient. Such samples include, but are not limited to, tissue, cells, blood, serum, cerebrospinal fluid, urine, cell lysate, plasma, excrement, sputum, blood cells, fine needle biopsy samples, peritoneal fluid, and pleural fluid, or cells therefrom. Biological samples may also include sections of tissues such as frozen sections taken for histological purposes.

In certain embodiments the present invention relates to a method wherein the biological sample is selected from a group consisting of tissue, cells, blood, serum, cerebrospinal fluid, urine, cell lysate, plasma, excrement, sputum, blood cells, fine needle biopsy samples, peritoneal fluid, and pleural fluid, or cells therefrom.

The term "test sample", as used herein, refers to a sample obtained from non-living sources. Sources of test samples include, but are not limited to, foods, drinks, soils, ground water, seawater, and lake marsh water. Pathogens and cells infected by pathogens are usually contained in these test samples.

The pathogens of biological samples and test samples are identified by the presence or absence of target nucleic acids of the particular pathogens. In certain embodiments the target nucleic acid includes genomic material, mitochondrial DNA, rRNA, tRNA, mRNA, viral RNA, plasmid DNA, and fragments thereof of the pathogens.

Pathogens are classified into a plurality of groups depending on the symptom and the infection route. A plurality of kinds of target nucleic acid detecting reagents and oligonucleotide microarrays are prepared so as to correspond to a plurality of groups. A target nucleic acid detecting reagent and an oligonucleotide microarray, which are selected depending on the symptom, are used. Therefore, among pathogens which are predicted from the symptom and the infection route, true pathogens can be identified with high accuracy.

III. Target Nucleic Acids

A target nucleic acid is a polynucleotide inherent to a pathogen that is to be detected. The polynucleotide is genetic material including genomic DNA/RNA, mitochondrial DNA, rRNA, tRNA, mRNA, viral RNA, and plasmid DNA. By detecting the presence of a target nucleic acid that is unique to a pathogen, the presence of the pathogen itself can be inferred. Similarly, the presence of a target nucleic acid that is specific to a genus of pathogens indicates the presence of a member of the genus.

The terms "nucleotide sequence" or "nucleic acid" or "polynucleotide" are used interchangeably and refer to a heteropolymer of nucleotides or the sequence of these nucleotides. An "oligonucleotide" refers to a polynucleotide of about 50 nucleotides or less. These terms also refer to DNA or RNA which may be single-stranded or double-stranded and may represent the sense or the antisense strand to a cDNA. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil).

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The terms "purified" or "substantially purified" as used herein denotes that the indicated nucleic acid or polypeptide is present in the substantial absence of other biological macromolecules, e.g., polynucleotides, proteins, and the like.

The term "isolated" as used herein refers to a nucleic acid separated from at least one other component present with the nucleic acid in its natural source. In one embodiment, the nucleic acid is found in the presence of (if anything) only a solvent, buffer, ion, or other component normally present in a solution of the same. The terms "isolated" and "purified" do not encompass nucleic acids present in their natural source.

As used herein, "substantially equivalent" or "substantially similar" refers to nucleotide sequences that vary from a reference sequence by one or more substitutions, deletions, or additions, the net effect of which does not result in an adverse functional dissimilarity between the reference and subject sequences. Typically, such a substantially equivalent sequence varies by no more than about 35% (i.e., the number of individual nucleotide substitutions, additions, and/or deletions in a substantially equivalent sequence, as compared to the corresponding reference sequence, divided by the total number of nucleotides in the substantially equivalent sequence is about 0.35 or less). Such a sequence is said to have 65% sequence identity to the listed sequence. In one embodiment, a substantially equivalent sequence of the invention varies from a reference sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). In one embodiment, the nucleotide sequence has at least about 65% identity. In other embodiments, the nucleotide sequence has at least about 75%, 80%, 85%, 90%, 95%, 98%, or 99% identity.

In certain aspects, the present invention relates to preparing a "target nucleic acid detecting reagent". The target nucleic acid detecting reagent can either be the target nucleic acid itself or an amplified target nucleic acid.

Target nucleic acids are isolated from biological samples and test samples using standard techniques. The technique used will be determined by what type of polynucleotide is to be isolated, DNA or RNA. Isolation techniques also can be modified depending on the type of pathogen being investigated and quantity of biological/test sample.

IV. Detecting Reagents

In certain embodiments the target nucleic acid is amplified to generate a "target nucleic acid detecting reagent" before hybridization to the oligonucleotide microarray. In other embodiments the target nucleic acid is not amplified before hybridization to the oligonucleotide microarray and the "target nucleic acid detecting reagent" and the target nucleic acid are one in the same. In one embodiment, the target nucleic acid or amplified target nucleic acid is labeled with one or more marker molecules. The attachment of a marker molecule facilitates detection of the target nucleic acid or amplified target nucleic acid upon hybridization to the oligonucleotide microarray. The marker molecules may be incorporated by any of a number of means well known to those of skill in the art. In one embodiment, the marker molecules are simultaneously incorporated during the amplification step in the preparation of the target nucleic acids of the sample. Thus, for example, polymerase chain reaction (PCR) with primers or nucleotides comprising marker molecules will provide an amplification product containing marker molecules. In certain embodiments the marker molecule comprises biotin, a magnetic bead, a fluorescent dye, a radiolabel, an enzyme, a colorimetric label, colored glass, or a plastic bead. In one embodiment, transcription amplification, as described above, using a nucleotide comprising a marker molecule (e.g. fluorescein-labeled UTP and/or CTP) incorporates a label into the transcribed nucleic acids.

Alternatively, a marker molecule may be added directly to the original target nucleic acid (e.g., mRNA, polyA, mRNA, cDNA, etc.). Means of attaching marker molecule to nucleic acids are well known to those of skill in the art and include, for example nick translation or end-labeling by phosphorylation of the target nucleic acid via kinase reaction the and subsequent attachment (ligation) of a nucleic acid linker joining the sample nucleic acid to a marker molecule.

Detectable marker molecules suitable for use in the present invention include any composition detectable by spectroscopic, photochemical, biochemical, immunochemical, electrical, optical or chemical means. Useful marker molecules in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. In one embodiment the marker molecule is a nucleotide comprising a marker molecule that is incorporated into an amplified target nucleic acid.

A nucleotide comprising a marker molecule can be a nucleotide (monomer) labeled with a fluorescent substance (Cy3, Cy5 etc.) or biotin because it has a high detecting sensitivity and is easily handled. A nucleotide comprising a marker molecule is taken into a polynucleotide to be amplified by the PCR reaction, and labels the amplified polynucleotide. In the case of a nucleotide labeled with biotin, a labeled polynucleotide is visualized by enzyme-linked immunosorbent assay (ELISA).

In certain embodiments, the present invention comprises an amplifying step of amplifying the target nucleic acid by PCR reaction, and a gene detecting step of detecting whether a polynucleotide comprising a target nucleic acid is present in the amplified PCR reaction product. In the gene detecting step, for example, the presence of a polynucleotide is detected using an oligonucleotide microarray.

V. Target Nucleic Acid Amplification Step

In certain embodiments the target nucleic acid detecting reagent is produced by amplification of the target nucleic acid. In one embodiment the target nucleic acid detecting reagent is amplified using PCR. In the target nucleic acid amplification step, the PCR reaction is performed using a sample extract, a gene detecting primer reagent for amplifying a polynucleotide comprising a target nucleic acid, and a labeling nucleotide. The sample extract is an extract obtained by extracting and purifying a polynucleotide contained in a test sample according to known polynucleotide extracting methods for extracting and purifying a DNA or an RNA, and is utilized as a template in the PCR reaction.

A nucleic acid is substantially identical to a second nucleic acid when both nucleic acids hybridize to the same probe nucleic acid under stringent conditions. Homology between substantially identical nucleic acids can be 80%, 90%, 95% or more.

In order to perform a gene amplifying step, a sample extract, a pathogen identifying primer reagent, a labeled nucleotide and other reagents and enzymes necessary for the PCR reaction are PCR-reacted in one reaction tube. By the PCR reaction, a polynucleotide is amplified.

Frequently, it is desirable to amplify the nucleic acid sample prior to hybridization to the oligonucleotide microarray. Suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4:560 (1989), Landegren, et al., Science, 241:1077 (1988) and Barringer, et al., Gene, 89:117 (1990), transcription amplification (Kwoh, et al., Proc. Natl. Acad. Sci. USA, 86:1173 (1989)), and self-sustained sequence replication (Guatelli, et al., Proc. Nat. Acad. Sci. USA, 87: 1874 (1990)). In one embodiment, the target nucleic acid is amplified by using PCR. In another embodiment, the target nucleic acid is amplified by using reverse transcriptase (RT)-PCR. In a further embodiment RT-PCR is performed using Tth DNA Polymerase (available from, for example, Promega (Cat. No. M210A)). Tth DNA Polymerase is a recombinant form of the enzyme obtained from the *thermophilic eubacterium Thermus thermophilus* HB-8 and is a thermostable enzyme that replicates DNA at 74° C. and exhibits a half-life of 20 minutes at 95° C. Tth DNA Polymerase catalyzes the polymerization of nucleotides into duplex DNA in the 5'→3' direction in the presence of magnesium and the polymerization of nucleotides into DNA using an RNA template in the 5'→3' direction in the presence of manganese. Tth DNA Polymerase is often used in PCR, RT-PCR, reverse transcription and primer extension reactions at elevated temperature.

The amplification methods of the invention employ the following enzymatic activities: DNA polymerase and DNA dependent RNA polymerase. DNA polymerases for use in the methods and compositions of the present invention are capable of effecting extension of the primer according to the methods of the present invention. Accordingly, a selected polymerase is one that is capable of extending a nucleic acid primer along a target nucleic acid template that is comprised at least predominantly of deoxyribonucleotides. The polymerase is able to displace a nucleic acid strand from the polynucleotide to which the displaced strand is bound.

Any reverse transcriptase may be used in the practice of the invention, including, but not limited to, Superscript RTII, "regular" MMLV-RT, AMV RT, or combinations thereof.

When a predicted pathogen is not present in the sample extract, and when a polynucleotide is not present in the sample extract, the amplified polynucleotide is not present in the PCR reaction product, and a polynucleotide is not detected in the subsequent gene detecting step.

When a predicted pathogen is present in the sample extract, a polynucleotide derived from that pathogen functions as a template in the PCR reaction. The PCR reaction proceeds by binding of the corresponding amplifying primer in a pathogen identifying primer reagent to the template, whereby a polynucleotide comprising a target nucleic acid inherent to a pathogen is amplified. A labeling nucleotide is taken into the amplified polynucleotide (DNA), that is, the PCR reaction product. Therefore, the PCR reaction product is labeled.

The primers used to amplify the target nucleic acid are designed based on polynucleotides isolated from a pathogen selected from the group consisting of bacteria, viruses, fungi, and protozoa. In other embodiments, the primers used to amplify the target nucleic acid are designed based on polynucleotides isolated from *rickettsia, chlamydia, mycoplasma, spirochete, streptococcus, salmonella, staphylococcus, mycoplasma, L. monocytogenes, N. meningitides, E. coli, H. influenzae, B. burgdorferi, leptospira, proteus, anaerobacter, M. tuberculosis, enterococcus*, poliovirus 1, enterovirus 71, enterovirus 70, echovirus 2, echovirus 4, echovirus 6, echovirus 9, echovirus 11, echovirus 12, echovirus 26, coxsackievirus A13, coxsackievirus A15, coxsackievirus A18, coxsackievirus A20, coxsackievirus A21, coxsackievirus B3-A, coxsackievirus B3-C, HSV-1, and HSV-2. In some embodiments the PCR utilizes a primer comprising a polynucleotide sequence isolated from at least one of the pathogens listed above.

Figure 2A:
Figure 3:
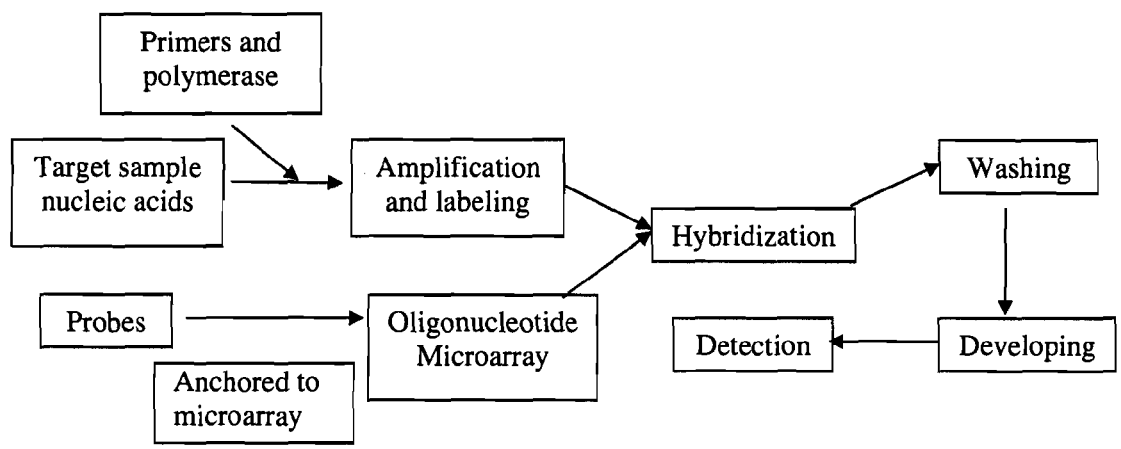
FIG. 3 is a schematic view of an embodiment of the present invention.

In certain embodiments a particular primer pair is capable of annealing to polynucleotides of more than one pathogen. Such a primer pair would anneal to regions that are conserved in certain pathogens. However, the nucleotide sequence that the primer pair flanks is a variable region. Use of such a primer pair allows nucleic acid sequences of multiple pathogens to be amplified, but yet still allows these pathogens to be differentiated upon hybridization to the oligonucleotide microarray. Two identical regions from the 16S/18S rDNA gene of many bacteria and fungi, when used as primers, provide a 197 base pair (bacteria) or 248 base pair (fungi) DNA segment by PCR amplification. Multiple low conservation regions are found in the DNA segment between the primer regions providing probes to discriminate the pathogens by hybridization according to their specific sequence. See FIGS. 1A and 1B, which show bacteria DNA sequences of 16S rDNA. The two conserved primer regions are shown, with a variable probe region between the conserved regions. FIGS. 2A and 2B show the primer and probe regions in the 18S rDNA segment of fungi DNA sequences.

In one embodiment the PCR utilizes a primer comprising a polynucleotide selected from the group consisting of SEQ ID NO: 1-12 (Table 1). Some combinations of primer pairs include SEQ ID NOS: 1 and 2; SEQ ID NOS: 1 and 4; SEQ ID NOS: 1 and 6; SEQ ID NOS: 3 and 2; SEQ ID NOS: 3 and 4; SEQ ID NOS: 3 and 6; SEQ ID NOS: 5 and 2; SEQ ID NOS: 5 and 4; SEQ ID NOS: 5 and 6; SEQ ID NOS: 5 and 6; SEQ ID NOS: 7 and 8; SEQ ID NOS: 9 and 10 and/or SEQ ID NOS: 11 and 12.

TABLE 1

| Primer source | Sequence (5'→3') | SEQ ID NO |
|---|---|---|
| Bacteria+ | actcctacgggaggcagcag | 1 |
| Bacteria− | attaccgcggctgctggcac | 2 |
| Bacteria+ | ccagactcctacgggaggcagcag (353) | 3 |
| Bacteria− | gattaccgcggctgctggcac (553) | 4 |
| Bacteria+ | ccatactcctacgggaggcagcag (353) | 5 |
| Bacteria− | tattaccgcggctgctggcac (553) | 6 |
| Enteroviruses: | ctccggcccctgaatgcgg (372) | 7 |
| Enteroviruses: | acccaaagtagtcggttccg (478) | 8 |
| HSVs | ggaactcctccaccgccca (74869) | 9 |
| HSVs | gtaccagggcgtcctgggc (75086) | 10 |
| Fungus | ggccgttcttagttggtggagt | 11 |
| Fungus | atgctctatcccagcacgac | 12 |

The numbers after the sequences refer to the nucleotide position to which the primers anneal on the various templates.

VI. Microarrays

A "microarray" is a linear or two-dimensional microarray of discrete regions, each having a defined area, formed on the surface of a solid support. An oligonucleotide probe microarray complementary to the target nucleic acid sequence or subsequence thereof is immobilized on a solid support using one of the display strategies described below. The methods of this invention employ oligonucleotide microarrays which comprise probes exhibiting complementarity to one or more target nucleic acid sequences. Typically, these probes are DNA and are immobilized in a high density microarray (i.e., a "DNA chip") on a solid surface. Essentially, any conceivable substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is generally flat but may take on a variety of alternative surface configurations. For example, the substrate may contain raised or depressed regions on which the synthesis takes place. The substrate and its surface can form a rigid support on which to carry out the reactions described herein. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In one embodiment the substrate is flat glass.

Various strategies are available to order and display the oligonucleotide probe microarrays on the substrate and thereby maximize the hybridization pattern and sequence information derivable regarding the target nucleic acid. Exemplary display and ordering strategies are described in PCT patent publication No. WO 94/12305, incorporated herein by reference.

The probes can be oligodeoxyribonucleotides or oligoribonucleotides, or any modified forms of these nucleotide polymers that are capable of hybridizing with a target nucleic sequence by complementary base-pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the chemistry for solid phase synthesis of oligonucleotides. A multitude of a single probe is immobilized in a discrete location on the substrate so as to differentiate hybridization of the target nucleic acid detecting reagent to each type of probe. Each discrete multitude of a single probe is referred to as a "spot". The spot size can be around 0.7 mm to 1 mm in diameter, with 0.35 uM to 40 uM DNA in each spot. For example, a DNA microarray that tests for the presence polynucleotides of two pathogens: *streptococcus* and *salmonella* would have two spots: one consisting of *streptococcus* probes, the other consisting of *salmonella* probes. In certain embodiments, 6, 12, 24, 36, 56, 64, 96, 108, or 384 different spots of probes are fixed on one substrate. In one embodiment the microarray can be 1.5 cm$^2$.

In some microarrays, all probes are the same length. Other microarrays employ probes of different lengths. The lengths of the probes can be varied in order to optimize particular hybridization conditions. Hybridization conditions are optimized to reduce "noise". Hybridization conditions are modified by altering the pH, temperature, and ionic conditions of the hybridization reaction. The term "stringent" is used to refer to conditions that are commonly understood in the art as requiring high complementarity between nucleic acid sequences in order for hybridization to occur. Stringent conditions can include highly stringent conditions, i.e., hybridization in 0.5 M NaHPO$_4$, 7% sodium dodecyl sulfate (SDS), 1 mM EDTA at 65° C. In instances of hybridization of oligonucleotides, additional exemplary stringent hybridization conditions include washing in 6×SSC/0.05% sodium pyrophosphate at 37° C. Higher temperatures such as 48° C., 55° C., 60° C., and 64° C. can be used for longer oligonucleotides.

In another embodiment the present invention relates to a method that further comprises washing the oligonucleotide microarray and detecting the presence of the marker molecule. For example, washing can be performed in 0.1×SSC/0.1% SDS at 68° C.), and under moderately stringent conditions (i.e., washing in 0.2×SSC/0.1% SDS at 42° C.).

In some embodiments, the probes are designed to be complementary to polynucleotides isolated from a pathogen selected from the group consisting of bacteria, viruses, fungi, protozoa. In other embodiments, the probes are designed to be complementary to polynucleotides isolated from *rickettsia, chlamydia, mycoplasma, spirochete, streptococcus, salmonella, staphylococcus, mycoplasma, L. monocytogenes, N. meningitides, E. coli, H. influenzae, B. burgdorferi, leptospira, proteus, anaerobacter, M. tuberculosis, enterococcus,* poliovirus 1, enterovirus 71, enterovirus 70, echovirus 2, echovirus 4, echovirus 6, echovirus 9, echovirus 11, echovirus 12, echovirus 26, coxsackievirus A13, coxsackievirus A15, coxsackievirus A18, coxsackievirus A20, coxsackievirus A21, coxsackievirus B3-A, coxsackievirus B3-C, HSV-1, and HSV-2. In another embodiment, the probes are selected from the group consisting of SEQ ID NO: 13-52 (Table 2).

TABLE 2

| Probe source | Sequence (5'→3') | SEQ ID NO |
|---|---|---|
| *Streptococcus* | ccgagcaacgccgcgtgagtgaagaaggttttcggatc | 13 |
| *Salmonella* | tgcagccatgccgcgtgtatgaagaaggccttcgggtt | 14 |
| *Salmonella* | tttttccccggggaggaaggtgttgtggttaata | 15 |
| *Salmonella* | tttttcccgtgttgtggttaataaccgcagcaa | 16 |
| *Salmonella* | cccccgtactttcagcggggaggaaggtgttgtggttaat | 17 |
| *Staphylococcus* | cggagcaacgccgcgtgagtgatgaaggtcttcggatc | 18 |
| *Mycoplasma* | tgaagcaatgccgcgtgagtgatgacggccttcgggtt | 19 |
| *L. monocytogenes* | cggagcaacgccgcgtgtatgaagaaggttttcggatc | 20 |
| *N. meningitides* | tccagccatgccgcgtgtctgaagaaggccttcgggtt | 21 |
| *E. coli* | tgcagccatgccgcgtgtatgaagaaggccttcgggtt | 22 |
| *E. coli* | gaagggagtaaagttaatacctttgctcattgacg | 23 |
| *E. coli* | tttttccccggggaggaagggagtaaagttaata | 24 |
| *E. coli* | cgtcaatgagcaaaggtattaactttactccctt | 25 |
| *E. coli* | cccccgtcaatgagcaaaggtattaactttactccctt | 26 |
| *H. influenzae* | cgcagccatgccgcgtgaatgaagaaggccttcgggtt | 27 |
| *B. burgdorferi* | cggagcgacactgcgtgaatgaagaaggtcgaaagatt | 28 |
| *Leptospira* | agcagcgacgccgcgtgaacgatgaaggtcttcggatt | 29 |
| *Proteus* | tgcagccatgccgcgtgtatgaagaaggccttagggtt | 30 |
| *Anaerobacter* | tgcagcaacgccgcgtgagtgataaggcttcgggttgt | 31 |
| *M. tuberculosis* | tgcagcgacgccgcgtgggggatgacggccttcgggtt | 32 |

TABLE 2-continued

| Probe source | Sequence (5'→3') | SEQ ID NO |
|---|---|---|
| Enterococcus | ccgagcaacgccgcgtgagtgaagaaggttttcggatc | 33 |
| Poliovirus 1 | ccacggagcaagtgccctcaatccagagggtggctt | 34 |
| Enterovirus 71 | ctgcggagcacatgctcacaaaccagtgggtggtgt | 35 |
| Enterovirus 70 | ccatggagcaaatgctcacaatccagtgagtggttt | 36 |
| Echovirus 2 | ctgcggagcaggtacccacgagccagtgggcagcct | 37 |
| Echovirus 4 | ctgcggagcacacgctcacaagccagtgagtggtgt | 38 |
| Echovirus 6 | ctgcggagcaggtgctcacaatccagtgggtggcct | 39 |
| Echovirus 9 | ctgtggagcacatgccctaatccaagggtagtgt | 40 |
| Echovirus 11 | ctgcggagcacatacccctaatccaagggcagtgt | 41 |
| Echovirus 12 | ctgtggagcaagtgcccacaacccagtgggtggctt | 42 |
| Echovirus 26 | ctgcggagcaggcacccacaagccagtgggcagcct | 43 |
| Coxsackievirus A13 | ccatggagcaagtgatcacaatccagtgatattctt | 44 |
| Coxsackievirus A15 | ccacggagcaggtgacttcaagccagaagttggcct | 45 |
| Coxsackievirus A18 | ccacggagcaagtgctcacgaaccagtgagtggctt | 46 |
| Coxsackievirus A20 | ccatggagcaggcggtcacagaccagtgactagctt | 47 |
| Coxsackievirus A21 | ccacggagcaaccgctcacaacccagtgagtaggtt | 48 |
| Coxsackievirus B3-A | ctgtggatcatgcgccctcaaaccagagggaagcgt | 49 |
| Coxsackievirus B3-C | ctgcggagcatgcacccacaagccagtgggtagcgt | 50 |
| HSV-1 | gttgggccacgcgcccccgagctggtggacggcccgg | 51 |
| HSV-2 | gcttggtgacgcgcgcccagctcctccacggcctccg | 52 |

Several technologies have been developed to design, synthesize, hybridize and interpret high density oligonucleotide microarrays of the type described above.

Light directed synthesis can be used to build oligonucleotide probes on the surface of the substrate (Fodor, et al., Science, 251:767-73 (1991)). This light-directed synthesis combines semiconductor based photolithography and solid phase chemical synthesis. The process begins when linkers modified with photochemically removable protecting groups are attached to a solid substrate, the substrate surface. Linkers and phosphoramidites with photolabile protecting groups have been synthesized and are described by Pease, et al., PNAS, 91:11241-11245 (1994). Light is directed through a photolithographic mask to specific areas of the synthesis surface, activating those areas for subsequent chemical coupling. The first of a series of nucleotides possessing photolabile protecting groups, is incubated with the substrate and chemical coupling occurs at those sites which have been illuminated in the preceding step. Light is then directed through a different section of the mask to the next synthesis site and the chemical steps, a defined collection of oligonucleotide probes can be constructed, each having its own unique address on the surface of the substrate. Oligonucleotide microarrays hybridized to amplification-generated fluorescently-labeled DNA or RNA and the hybridizations are detected by epi-fluorescence confocal microscopy (Fodor, et al., 1993).

In one embodiment, the oligonucleotide microarray has spots containing all probes inherent to each pathogen to be tested.

Accordingly, the present invention relates to method for detecting a target nucleic acid of a pathogen in a biological sample or a test sample. The method comprises preparing a target nucleic acid detecting reagent; and contacting the target nucleic acid detecting reagent with an oligonucleotide microarray. In some embodiments the pathogen is selected from the group consisting of *streptococcus, salmonella, staphylococcus, mycoplasma, L. monocytogenes, N. meningitides, E. coli, H. influenzae, B. burgdorferi, leptospira, proteus, anaerobacter, M. tuberculosis, enterococcus*, poliovirus 1, enterovirus 71, enterovirus 70, echovirus 2, echovirus 4, echovirus 6, echovirus 9, echovirus 11, echovirus 12, echovirus 26, coxsackievirus A13, coxsackievirus A15, coxsackievirus A18, coxsackievirus A20, coxsackievirus A21, coxsackievirus B3-A, coxsackievirus B3-C, HSV-1, and HSV-2. In some embodiments, the oligonucleotide microarray comprises a probe said probe comprising a polynucleotide sequence isolated from at least one of these enumerated pathogens. In another embodiment, the probe comprises a polynucleotide sequence selected from the group consisting of SEQ ID NO: 13-52.

VII. Kits

In certain aspects the present invention also relates to a kit for detecting a target nucleic acid of a pathogen in a test sample. The kit comprises at least one primer pair, and an oligonucleotide microarray comprising at least one probe. In one embodiment the primer pair comprises a primer selected from the group consisting of SEQ ID NO: 1-12. In another embodiment the probe comprises a polynucleotide sequence selected from the group consisting of SEQ ID NO: 13-52.

The present invention will be explained in more detail by way of the following Examples. The present examples and embodiments are to be considered as illustrative and not restrictive and the invention is not to be limited to the details given herein, but may be modified within the scope and equivalence of the appended claims.

VIII. Examples

Example 1

DNA Microarray Fabrication Process
1. Glass Surface Washing.
   Clear slide immersed in $H_2SO_4/H_2O_2$, 2:1 for 30 min. Wash with $H_2O$ three times, and then with methanol for twice. Dry under a stream of pressed air, then baked at 80° C. for 10 min.
2. Glass Silanization.
   Sonicated in 2% N-(2-aminoethyl)-3-aminopropyltrimethoxysilane (EDA) in 1 mM HAc for 30 min at room temperature (RT). Wash with $H_2O$ three times, and then with methanol for twice. Dry under a stream of $N_2$, then baked at 110° C. for 15 min.
3. Modify Silanized Slide with Heterobifunctional Crosslinker
   Immersed in the crosslinker solution (384 mg PDITC (2 mmol) in 80 ml 10% anhydrous pyridine in DMF) for 2 hr at RT. Rinsed with the DMF three times and then dichloroethane twice. Dry under $N_2$.
4. Microarray Print and DNA Immobilization
   Spot 40 uM $NH_2$-oligodeoxynucleotide (ODN) in 0.1M carbonate buffer (pH 9.0) on the active glass slide at 60% humidity. React over 1 hr at 37° C. under saturated humidity. Rinsed with water and submerged in a solution containing 6-aminohexanol (100 mM) in $H_2O$. Washed $H_2O$ at 100° C. for 2-3 min, then dry under pressed air.

Example 2

DNA Microarray Hybridization Process

1. PCR Amplification and Labeling
   Add 1 ul DNA sample to 100 ul PCR reaction buffer, which contains 10 mM Tris-HCl (pH 9.0), 50 mM KCl, 3.75 mM $MgCl_2$, 0.1% Triton X-100, 0.1 mM dNTP (each), and 0.2 uM Cy5 labeled primers (each). Then add 5 u Tag DNA Polymerse and PCR amplified at the following temperature condition:

i). 96° C. 2 min
   ii). 95° C. 20 s
   iii). 60° C. 20 s
   iv). 72° C. 30 s
   Go to step ii for 28 cycles.
   v). 72° C. 2 min
   The reaction takes about 1 hr and 20 min total.
2. DNA Microarray Hybridization
   Dilute the PCR solution with 5 volumes hybridization buffer which contain 0.75M NaCl, 75 mM sodium citrate, and 0.1% SDS pH 7.2. Hybridization at 61° C. for 1 hr.
3. DNA Microarray Washing
   Wash the hybridized slide with 0.3M NaCl, 30 mM sodium citrate, and 0.1% SDS for 15 min for 3 times at 50° C., then wash with 0.3M NaCl, 30 mM sodium citrate, for 15 min at 50° C. Rinse with $H_2O$ then dry under pressed air.
4, Microarray Reading
   DNA microarray hybridization result is read by FuJiFilm™ fluorescent Scanner FLA3000, Cy5 is excited with HeNe Laser (633 nm). And the signal density is analysis with the packed software ArrayGuage™

Example 3

Cells are harvested directly from sections of tissue isolated from a patient. DNA is extracted from these cells using any known protocol. About 2-10 ng of DNA is amplified via PCR using two primer pairs: SEQ ID NOS: 1-2 and SEQ ID NOS: 7-8. [$^{32}$P]-dCTP is included in the PCR reaction in order to label the amplified DNA, thus generating target nucleic acid detecting reagents with marker molecules.

The target nucleic acid detecting reagents with marker molecules are purified via spin column in order to remove excess [$^{32}$P]-dCTP and denatured by incubation at 95° C. followed by immediate cooling on ice. The denatured target nucleic acid detecting reagents with marker molecules are then incubated under highly stringent conditions in the presence of an oligonucleotide microarray that comprises probes

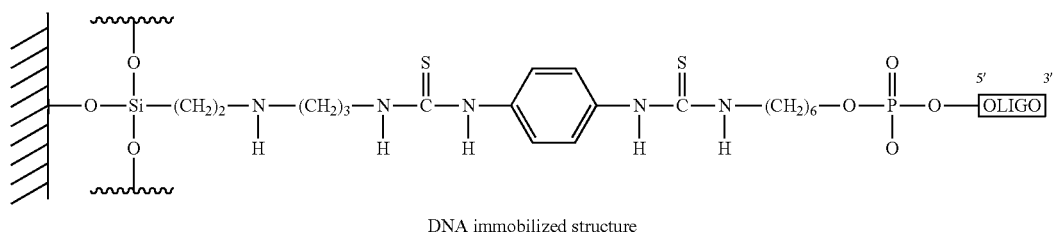

DNA immobilized structure comprising SEQ ID NOS: 13-52. The hybridization is for 2 hours in 0.5 M $NaHPO_4$, 7% sodium dodecyl sulfate (SDS), 1 mM EDTA at 65° C., followed by 3 washes in 0.1×SSC/0.1% SDS at 68° C. The microarray is exposed to X-ray film and an autoradiogram is developed.

Example 4

A drinking water sample is isolated from any typical drinking water source, e.g., from the reservoir or from the tap. The sample is concentrated and/or is filtered to isolate any pathogens. DNA is extracted from these cells using any known protocol. About 2-10 ng of DNA is amplified via PCR using two primer pairs: SEQ ID NOS: 1-2 and SEQ ID NOS: 7-8. [$^{32}$P]-dCTP is included in the PCR reaction in order to label the amplified DNA, thus generating target nucleic acid detecting reagents with marker molecules.

The target nucleic acid detecting reagents with marker molecules are purified via spin column in order to remove excess [$^{32}$P]-dCTP and denatured by incubation at 95° C. followed by immediate cooling on ice. The denatured target nucleic acid detecting reagents with marker molecules are then incubated under highly stringent conditions in the presence of an oligonucleotide microarray that comprises probes comprising SEQ ID NOS: 13-52. The hybridization is for 2 hours in 0.5 M NaHPO$_4$, 7% sodium dodecyl sulfate (SDS), 1 mM EDTA at 65° C., followed by 3 washes in 0.1×SSC/ 0.1% SDS at 68° C. The microarray is exposed to X-ray film and an autoradiogram is developed.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

SEQUENCE LISTING

<160> NUMBER OF SEQ ID NOS: 52

<210> SEQ ID NO 1
<211> LENGTH: 20
<212> TYPE: DNA
<213> ORGANISM: Bacterial

<400> SEQUENCE: 1
actcctacgg gaggcagcag                                          20

<210> SEQ ID NO 2
<211> LENGTH: 20
<212> TYPE: DNA
<213> ORGANISM: Bacterial

<400> SEQUENCE: 2
attaccgcgg ctgctggcac                                          20

<210> SEQ ID NO 3
<211> LENGTH: 24
<212> TYPE: DNA
<213> ORGANISM: Bacterial

<400> SEQUENCE: 3
ccagactcct acgggaggca gcag                                     24

<210> SEQ ID NO 4
<211> LENGTH: 21
<212> TYPE: DNA
<213> ORGANISM: Bacterial

<400> SEQUENCE: 4
gattaccgcg gctgctggca c                                        21

<210> SEQ ID NO 5
<211> LENGTH: 24
<212> TYPE: DNA
<213> ORGANISM: Bacterial

<400> SEQUENCE: 5
ccatactcct acgggaggca gcag                                     24

<210> SEQ ID NO 6
<211> LENGTH: 21
<212> TYPE: DNA
<213> ORGANISM: Bacterial

<400> SEQUENCE: 6
tattaccgcg gctgctggca c                                        21

<210> SEQ ID NO 7

```
<211> LENGTH: 19
<212> TYPE: DNA
<213> ORGANISM: Viral

<400> SEQUENCE: 7
ctccggcccc tgaatgcgg                                                19

<210> SEQ ID NO 8
<211> LENGTH: 20
<212> TYPE: DNA
<213> ORGANISM: Viral

<400> SEQUENCE: 8
acccaaagta gtcggttccg                                               20

<210> SEQ ID NO 9
<211> LENGTH: 19
<212> TYPE: DNA
<213> ORGANISM: Viral

<400> SEQUENCE: 9
ggaactcctc caccgccca                                                19

<210> SEQ ID NO 10
<211> LENGTH: 19
<212> TYPE: DNA
<213> ORGANISM: Viral

<400> SEQUENCE: 10
gtaccagggc gtcctgggc                                                19

<210> SEQ ID NO 11
<211> LENGTH: 22
<212> TYPE: DNA
<213> ORGANISM: Fungus

<400> SEQUENCE: 11
ggccgttctt agttggtgga gt                                            22

<210> SEQ ID NO 12
<211> LENGTH: 21
<212> TYPE: DNA
<213> ORGANISM: Fungus

<400> SEQUENCE: 12
atgctctatc cccagcacga c                                             21

<210> SEQ ID NO 13
<211> LENGTH: 38
<212> TYPE: DNA
<213> ORGANISM: Streptococcus

<400> SEQUENCE: 13
ccgagcaacg ccgcgtgagt gaagaaggtt ttcggatc                           38

<210> SEQ ID NO 14
<211> LENGTH: 38
<212> TYPE: DNA
<213> ORGANISM: Salmonella typhimurium

<400> SEQUENCE: 14
tgcagccatg ccgcgtgtat gaagaaggcc ttcgggtt                           38

<210> SEQ ID NO 15
```

```
<211> LENGTH: 34
<212> TYPE: DNA
<213> ORGANISM: Salmonella typhimurium

<400> SEQUENCE: 15
tttttccccg gggaggaagg tgttgtggtt aata                                34

<210> SEQ ID NO 16
<211> LENGTH: 34
<212> TYPE: DNA
<213> ORGANISM: Salmonella typhimurium

<400> SEQUENCE: 16
tttttccccg tgttgtggtt aataaccgca gcaa                                34

<210> SEQ ID NO 17
<211> LENGTH: 40
<212> TYPE: DNA
<213> ORGANISM: Salmonella typhimurium

<400> SEQUENCE: 17
cccccgtact ttcagcgggg aggaaggtgt tgtggttaat                          40

<210> SEQ ID NO 18
<211> LENGTH: 38
<212> TYPE: DNA
<213> ORGANISM: Staphylococcus

<400> SEQUENCE: 18
cggagcaacg ccgcgtgagt gatgaaggtc ttcggatc                            38

<210> SEQ ID NO 19
<211> LENGTH: 38
<212> TYPE: DNA
<213> ORGANISM: Mycoplasma

<400> SEQUENCE: 19
tgaagcaatg ccgcgtgagt gatgacggcc ttcgggtt                            38

<210> SEQ ID NO 20
<211> LENGTH: 38
<212> TYPE: DNA
<213> ORGANISM: Listeria monocytogenes

<400> SEQUENCE: 20
cggagcaacg ccgcgtgtat gaagaaggtt ttcggatc                            38

<210> SEQ ID NO 21
<211> LENGTH: 38
<212> TYPE: DNA
<213> ORGANISM: N.meningitides

<400> SEQUENCE: 21
tccagccatg ccgcgtgtct gaagaaggcc ttcgggtt                            38

<210> SEQ ID NO 22
<211> LENGTH: 38
<212> TYPE: DNA
<213> ORGANISM: E.Coli

<400> SEQUENCE: 22
tgcagccatg ccgcgtgtat gaagaaggcc ttcgggtt                            38

<210> SEQ ID NO 23
```

```
<211> LENGTH: 35
<212> TYPE: DNA
<213> ORGANISM: Enterococcus Coli

<400> SEQUENCE: 23
gaagggagta aagttaatac ctttgctcat tgacg                              35

<210> SEQ ID NO 24
<211> LENGTH: 35
<212> TYPE: DNA
<213> ORGANISM: E. Coli

<400> SEQUENCE: 24
tttttccccc ggggaggaag ggagtaaagt taata                              35

<210> SEQ ID NO 25
<211> LENGTH: 34
<212> TYPE: DNA
<213> ORGANISM: E. Coli

<400> SEQUENCE: 25
cgtcaatgag caaaggtatt aactttactc cctt                               34

<210> SEQ ID NO 26
<211> LENGTH: 39
<212> TYPE: DNA
<213> ORGANISM: E. Coli

<400> SEQUENCE: 26 cccccccgtca atgagcaaag gtattaactt tactcccctt                        39

<210> SEQ ID NO 27
<211> LENGTH: 38
<212> TYPE: DNA
<213> ORGANISM: H. influenzae

<400> SEQUENCE: 27
cgcagccatg ccgcgtgaat gaagaaggcc ttcgggtt                           38

<210> SEQ ID NO 28
<211> LENGTH: 38
<212> TYPE: DNA
<213> ORGANISM: B.burgdorferi

<400> SEQUENCE: 28
cggagcgaca ctgcgtgaat gaagaaggtc gaaagatt                           38

<210> SEQ ID NO 29
<211> LENGTH: 38
<212> TYPE: DNA
<213> ORGANISM: Leptospira

<400> SEQUENCE: 29
agcagcgacg ccgcgtgaac gatgaaggtc ttcggatt                           38

<210> SEQ ID NO 30
<211> LENGTH: 38
<212> TYPE: DNA
<213> ORGANISM: Proteus mirabilis

<400> SEQUENCE: 30
tgcagccatg ccgcgtgtat gaagaaggcc ttagggtt                           38

<210> SEQ ID NO 31
```

```
<211> LENGTH: 38
<212> TYPE: DNA
<213> ORGANISM: Anaerobacter

<400> SEQUENCE: 31
tgcagcaacg ccgcgtgagt gataaggctt cgggttgt                              38

<210> SEQ ID NO 32
<211> LENGTH: 38
<212> TYPE: DNA
<213> ORGANISM: M. tuberculosis

<400> SEQUENCE: 32
tgcagcgacg ccgcgtgggg gatgacggcc ttcgggtt                              38

<210> SEQ ID NO 33
<211> LENGTH: 38
<212> TYPE: DNA
<213> ORGANISM: Enterococcus Coli

<400> SEQUENCE: 33
ccgagcaacg ccgcgtgagt gaagaaggtt ttcggatc                              38

<210> SEQ ID NO 34
<211> LENGTH: 36
<212> TYPE: DNA
<213> ORGANISM: Poliovirus 1

<400> SEQUENCE: 34
ccacggagca agtgccctca atccagaggg tggctt                                36

<210> SEQ ID NO 35
<211> LENGTH: 36
<212> TYPE: DNA
<213> ORGANISM: Enterovirus 71

<400> SEQUENCE: 35
ctgcggagca catgctcaca aaccagtggg tggtgt                                36

<210> SEQ ID NO 36
<211> LENGTH: 36
<212> TYPE: DNA
<213> ORGANISM: Enterovirus 70

<400> SEQUENCE: 36
ccatggagca aatgctcaca atccagtgag tggttt                                36

<210> SEQ ID NO 37
<211> LENGTH: 36
<212> TYPE: DNA
<213> ORGANISM: Echovirus 2

<400> SEQUENCE: 37
ctgcggagca ggtacccacg agccagtggg cagcct                                36

<210> SEQ ID NO 38
<211> LENGTH: 36
<212> TYPE: DNA
<213> ORGANISM: Echovirus 4

<400> SEQUENCE: 38
ctgcggagca cacgctcaca agccagtgag tggtgt                                36

<210> SEQ ID NO 39
```

```
<211> LENGTH: 36
<212> TYPE: DNA
<213> ORGANISM: Echovirus 6

<400> SEQUENCE: 39
ctgcggagca ggtgctcaca atccagtggg tggcct                                 36

<210> SEQ ID NO 40
<211> LENGTH: 36
<212> TYPE: DNA
<213> ORGANISM: Echovirus 9

<400> SEQUENCE: 40
ctgtggagca catgccccta atccaagggg tagtgt                                 36

<210> SEQ ID NO 41
<211> LENGTH: 36
<212> TYPE: DNA
<213> ORGANISM: Echovirus 11

<400> SEQUENCE: 41
ctgcggagca catacccta atccaagggg cagtgt                                  36

<210> SEQ ID NO 42
<211> LENGTH: 36
<212> TYPE: DNA
<213> ORGANISM: Echovirus 12

<400> SEQUENCE: 42
ctgtggagca agtgcccaca acccagtggg tggctt                                 36

<210> SEQ ID NO 43
<211> LENGTH: 36
<212> TYPE: DNA
<213> ORGANISM: Echovirus 26

<400> SEQUENCE: 43
ctgcggagca ggcacccaca agccagtggg cagcct                                 36

<210> SEQ ID NO 44
<211> LENGTH: 36
<212> TYPE: DNA
<213> ORGANISM: Coxsackievirus A13

<400> SEQUENCE: 44
ccatggagca agtgatcaca atccagtgat attctt                                 36

<210> SEQ ID NO 45
<211> LENGTH: 36
<212> TYPE: DNA
<213> ORGANISM: Coxsackievirus A15

<400> SEQUENCE: 45
ccacggagca ggtgacttca agccagaagt tggcct                                 36

<210> SEQ ID NO 46
<211> LENGTH: 36
<212> TYPE: DNA
<213> ORGANISM: Coxsackievirus A18

<400> SEQUENCE: 46
ccacggagca agtgctcacg aaccagtgag tggctt                                 36

<210> SEQ ID NO 47
```

```
<211> LENGTH: 36
<212> TYPE: DNA
<213> ORGANISM: Coxsackievirus A20

<400> SEQUENCE: 47
ccatggagca ggcggtcaca gaccagtgac tagctt                              36

<210> SEQ ID NO 48
<211> LENGTH: 36
<212> TYPE: DNA
<213> ORGANISM: Coxsackievirus A21

<400> SEQUENCE: 48
ccacggagca accgctcaca acccagtgag taggtt                              36

<210> SEQ ID NO 49
<211> LENGTH: 36
<212> TYPE: DNA
<213> ORGANISM: Coxsackievirus B3-A

<400> SEQUENCE: 49
ctgtggatca tgcgcctca aaccagaggg aagcgt                               36

<210> SEQ ID NO 50
<211> LENGTH: 36
<212> TYPE: DNA
<213> ORGANISM: Coxsackievirus B3-C

<400> SEQUENCE: 50
ctgcggagca tgcacccaca agccagtggg tagcgt                              36

<210> SEQ ID NO 51
<211> LENGTH: 39
<212> TYPE: DNA
<213> ORGANISM: human herpesvirus 1

<400> SEQUENCE: 51
gttgggccac gcgcccccg agctggtgga cggcccgg                             39

<210> SEQ ID NO 52
<211> LENGTH: 39
<212> TYPE: DNA
<213> ORGANISM: human herpesvirus 2

<400> SEQUENCE: 52
gcttggtgac gcgcgcgccc agctcctcca cggcctccg                           39
```

What is claimed is:

1. A method for detecting a target nucleic acid of two or more different pathogens in a biological sample from a patient, said method comprising:
    amplifying the target nucleic acids in the sample utilizing at least first and second primer pairs that bind conserved regions in two or more different pathogens, wherein the first and second primer pairs are SEQ ID NOS: 1-2, corresponding to gram-positive and gram-negative bacteria, respectively, and SEQ ID NOS: 7-8, corresponding to enteroviruses;
    contacting the amplified target nucleic acids with an oligonucleotide microarray, said microarray including two or more probes or sets of probes comprising polynucleotide sequences complementary to two or more different pathogens, wherein the probes comprise polynucleotide sequences selected from the group consisting of SEQ ID NOS: 13-21, corresponding to Streptococcus, Salmonella, Staphylococcus, Mycoplasma, L. monocytogenes, N. meningitides, and SEQ ID NOS: 23-52, corresponding to E. coli, H. influenzae, B. burgdorferi, Leptospira, Proteus, Anaerobacter, M. tuberculosis, Enterococcus, Poliovirus 1, Enterovirus 71, Enterovirus 70, Echovirus 2, Echovirus 4, Echovirus 6, Echovirus 9, Echovirus 11, Echovirus 12, Echovirus 26, Coxsackievirus A13, Coxsackievirus A15, Coxsackievirus A18, Coxsackievirus A20, Coxsackievirus A21, Coxsackievirus B3-A, Coxsackievirus B3-C, HSV-1, and HSV-2; and
    detecting binding of amplified target nucleic acids to the probes, wherein binding to a probe indicates the presence of the polynucleotide sequence to which the probe is complementary in the sample.

2. The method of claim 1, wherein two of said target nucleic acids are E. coli and Salmonella, and the probes are selected from the group consisting of SEQ ID NO: 14-17 for *Salmonella*, and 23-26 for *E. coli*.

3. The method of claim 1, wherein said biological sample is selected from the group consisting of tissue, cells, blood, serum, cerebrospinal fluid, urine, cell lysate, plasma, excrement, sputum, blood cells, fine needle biopsy samples, peritoneal fluid, and pleural fluid, or cells therefrom.

4. The method of claim 1, wherein the microarray includes probes for pathogens associated with a common symptom.

5. The method of claim 1, wherein the microarray includes probes for pathogens associated with a common infection route.

6. A method of detecting target nucleic acids of *E. coli* and/or *Salmonella* in a sample taken from a patient, the method comprising:
   amplifying nucleic acids in the patient sample utilizing one or more primer pairs that bind conserved regions in *E. coli* and *Salmonella*, wherein at least one primer pair is SEQ ID NOS: 1 and 2, wherein additional primer pairs are selected from the group consisting of SEQ ID NOS: 1-6;
   contacting the amplified nucleic acids with an oligonucleotide microarray, said microarray including two or more probes comprising polynucleotide sequences complementary to variable regions in *E. coli* and *Salmonella*, wherein at least one probe is selected from the group consisting of SEQ ID NOS: 14-17 corresponding to *Salmonella*, and at least one probe is selected from the group consisting of SEQ ID NOS: 23-26 corresponding to *E. coli*; and
   detecting binding of amplified nucleic acids to the probes, where binding to the at least one probe selected from the group consisting of SEQ ID NOS: 14-17 is an indication of the presence of *E. coli* in the sample, and binding to the at least one robe selected from the rou consisting of SEQ ID NOS: 23-26 is an indication of the presence of *Salmonella* in the sample.

7. A kit for detecting a target nucleic acid of at least one pathogen in a test sample, said kit comprising:
   at least first and second primer pairs that bind conserved regions in two or more different pathogens, wherein the first and second primer pairs are SEQ ID NOS: 1-2, corresponding to gram-positive and gram-negative bacteria, respectively, and SEQ ID NOS: 7-8, corresponding to enteroviruses;
   an oligonucleotide microarray including two or more probes or sets of probes comprising polynucleotide sequences complementary to two or more different pathogens, wherein the probes comprise polynucleotide sequences selected from the group consisting of SEQ ID NOS: 13-21, corresponding to *Streptococcus, Salmonella, Staphylococcus, Mycoplasma, L. monocytogenes, N. meningitides*, and SEQ ID NOS: 23-52, corresponding to *E. coli, H. influenzae, B. burgdorferi, Leptospira, Proteus, Anaerobacter, M. tuberculosis, Enterococcus*, Poliovirus 1, Enterovirus 71, Enterovirus 70, Echovirus 2, Echovirus 4, Echovirus 6, Echovirus 9, Echovirus 11, Echovirus 12, Echovirus 26, Coxsackievirus A13, Coxsackievirus A15, Coxsackievirus A18, Coxsackievirus A20, Coxsackievirus A21, Coxsackievirus B3-A, Coxsackievirus B3-C, HSV-1, and HSV-2; and
   wherein the probes are immobilized on a solid support.

8. The method of claim 6, wherein additional primer pairs are selected from the following pairs: SEQ ID NOS: 1 and 4; SEQ ID NOS: 1 and 6; SEQ ID NOS: 3 and 2; SEQ ID NOS: 3 and 4; SEQ ID NOS: 3 and 6; SEQ ID NOS: 5 and 2; SEQ ID NOS: 5 and 4; SEQ ID NOS: 5 and 6.

* * * * *